United States Patent
Matter et al.

[11] Patent Number: 5,369,975
[45] Date of Patent: Dec. 6, 1994

[54] METHOD AND APPARATUS FOR AUTOMATIC SELECTION OF CONTAINERS

[75] Inventors: Ulrich Matter, Wohlen; Rene Nunlist, Aarau; Heinz Burtscher, Zurich, all of Switzerland; Michael Mukrowsky, Leimen, Germany

[73] Assignee: Martin Lehmann, Wohlen, Switzerland

[21] Appl. No.: 917,118

[22] PCT Filed: Dec. 4, 1991

[86] PCT No.: PCT/CH91/00243
§ 371 Date: Aug. 31, 1992
§ 102(e) Date: Aug. 31, 1992

[87] PCT Pub. No.: WO92/10751
PCT Pub. Date: Jun. 25, 1992

[30] Foreign Application Priority Data
Dec. 6, 1990 [DE] Germany ............................... 4038993

[51] Int. Cl.[5] .......................................... G01N 33/44
[52] U.S. Cl. ...................................... 73/23.2; 73/31.03
[58] Field of Search .................... 73/23.2, 19.01, 31.03

[56] References Cited

U.S. PATENT DOCUMENTS

| | | | |
|---|---|---|---|
| 3,266,292 | 8/1966 | Bailey | 73/31.03 |
| 3,321,954 | 5/1967 | Bailey | 73/31.03 |
| 4,818,348 | 4/1989 | Stetter | 73/23.2 X |

*Primary Examiner*—Hezron E. Williams
*Assistant Examiner*—Joseph W. Roskos
*Attorney, Agent, or Firm*—Antonelli, Terry, Stout & Kraus

[57] ABSTRACT

In order to increase the reliability of detection of gaseous contamination in containers, gas (G) from the container is subject to several different methods of analysis (54a to 54d), each of which emits differing output signal courses ($I_1$ to $I_4$), depending on the contaminants and their concentration. A vector of the state vector type ($\overline{P}_{GAS}$) is formed with the output signals ($I_1$ to $I_4$) as a state variable and checked to see whether it defines a permissible or an unacceptable state of contamination (56). On the basis of this examination the decision is taken whether a container is acceptably or unacceptably contamined.

36 Claims, 7 Drawing Sheets

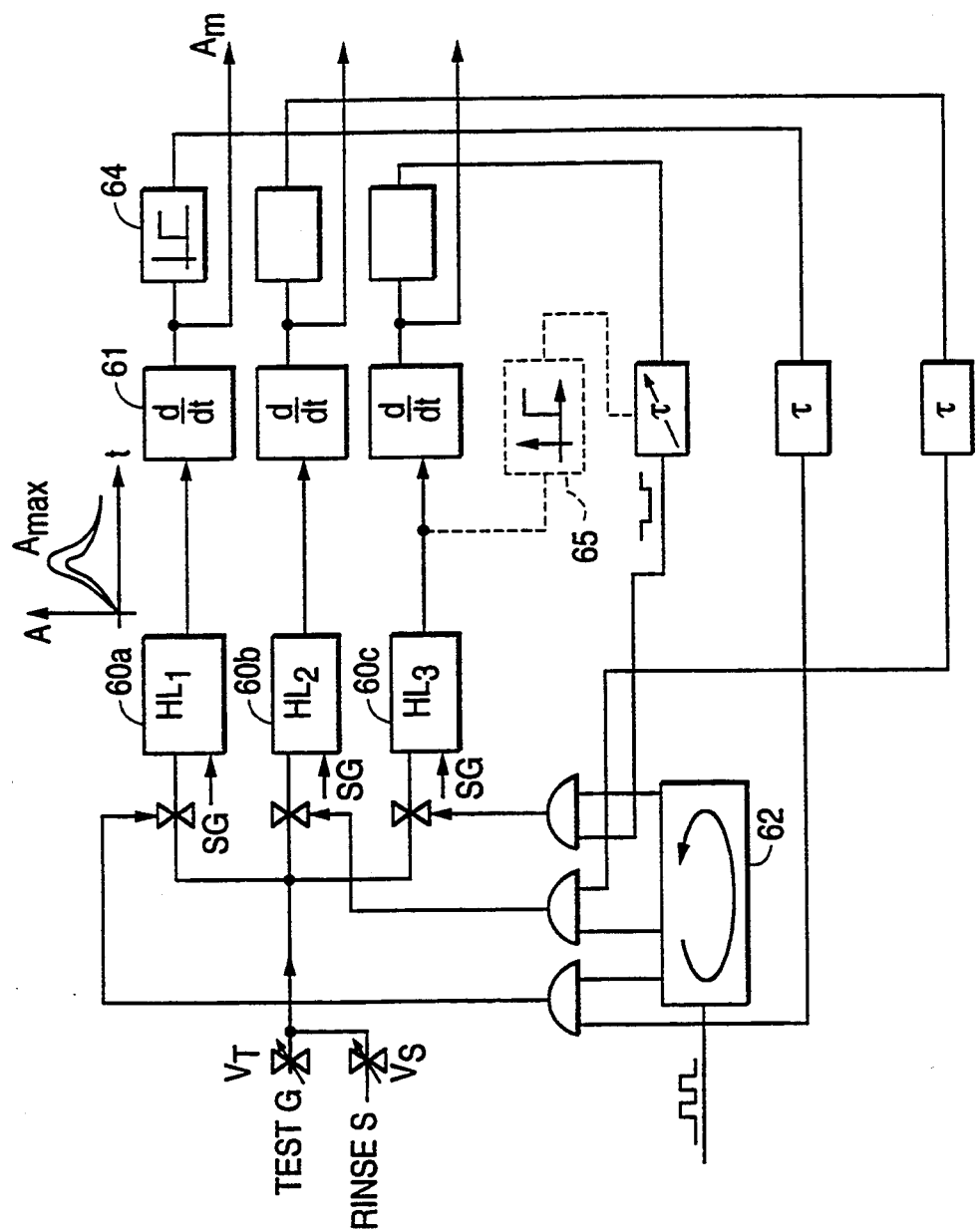

METHOD AND APPARATUS FOR AUTOMATIC SELECTION OF CONTAINERS

FIELD OF THE INVENTION

The present invention relates to a method and a measuring arrangement for the automatic selection of containers, depending on whether the containers or possibly their contents are contaminated with an admissible or an inadmissible group of contaminations, as well as to a plant with such a measuring arrangement.

BACKGROUND

From the EP-A-0 306 307, which herewith is declared an integral part of the present description, it is known, within the framework of the recycling of containers, to detect on empty containers, in particular plastic containers, e.g. plastic bottles, whether any contaminations are present inside the container.

To this end it is proposed to detect such contaminations with the aid of an ionization technique, e.g. flame ionization or photo ionization in the UV-range, and if need be to eliminate the contaminated containers before re-filling them.

From the WO88/00862 a selection method of containers is known, with which either distilled water is sprayed into the containers, water that may now be contaminated is removed from the containers and analysed, or water is sprayed into the containers, shaken in same and then analysed.

To increase the analysis redundancy, it is well known to use two different analysis techniques. The output signal of the detectors of the two analysis techniques is first of all compared with reference data, the comparison result is then compared with a correlation value range which depends on the specific analysis technique and a specific product which originally was present in the container.

On which basis the deciding correlation factors are determined according to this publication, is not indicated. Described is the use of detectors which specifically detect a given substance, e.g. a sugar analyser, and the providing of two such detectors that respond with a narrow band to a substance would make it possible to detect compound contaminations.

In principle, with regard to the technique described in the WO88/00862, it must be regarded as disadvantageous that liquid samples must be taken from the containers in question, so that the test method based thereon is extremely slow. On the other hand, because of the slowness resulting from the use of a liquid, there is sufficient time to test the liquid sample for contaminations under conditions that are practically similar to those in the laboratory.

SUMMARY OF INVENTION

The present invention proceeds from a method as described in the abovementioned EP-A-0 306 307, according to which gas from the containers is analysed. Already because of the flow properties of gas, compared to those of a liquid, the latter method results in a considerable shortening of the process cycles compared to the method of WO88/00862, which is particularly important for the selecting of containers that are fed to the line in quick succession.

Proceeding from such a gas analysis process, the present invention proceeds from the recognition of the problem that known analysis methods for gas analyses supply output signals that depend both on the contaminating substance that is being detected as well as on its concentration, i.e. on two variables. This causes ambiguity in the evaluation of such individually viewed signals. Often it is not possible to differentiate whether a detected output signal indicates a concentration $\alpha$ of the substance A or a concentration $\eta$ of the substance B. With a measuring operation tht is being considered, the concentration $\alpha$ of the substance A may provide the same result as the concentration $\beta$ of the substance B.

Under the aspect of reliability, it is the object of the present invention to solve this problem.

This is achieved with the method of the abovementioned type when one proceeds in accordance with the method of the invention, or with a suitable measuring arrangement in accordance with the invention.

In the method of the invention the gas analysis is carried out by means of n analysis techniques ($54a,b$ ...) with $n \geq 2$, each of which produces different output signal patterns ($I_1$ ...) as a function of the contamination substance as well as its concentration; at least one n-dimensional range (ZUL) with state variable ($I_1, I_2$ ...) corresponding to the output signals (I) for states of admissible contaminations is determined; and the analysis results of the analysis techniques ($I_1, I_2$ ...) are evaluated by checking whether they define a state in the admissible state range (ZUL).

The measuring arrangement of the invention comprises a detector arrangement for the analysis of gas from the containers, a comparator unit to which are connected the output of the detector arrangement and a reference signal storage unit. The detector arrangement comprises n detectors with $n \geq 2$, which generate different output signals ($I_1, I_2$ ...) as a function of the contamination substance and its concentration. The comparator unit compares the substance and concentration dependent output signals ($I_1, I_2$ ...) of the detectors with output signals of the storage unit associated with the detectors, which latter output signals depend on the admissibility of contamination substances and their concentration.

It was recognized that different gas analysis techniques give output signals that depend on the concentration and on the contaminating substance, respectively. These different output signals, because of the different analysis techniques, are linearly independent of one another in the sense that, for example, there does not exist a simple proportionality between the different signals. The transfer characteristics of the different gas analysis techniques are characteristically different in their dependence on the variables "substance" and "concentration". The term "output signal" in this connection denotes all signal parameters that can characterize a signal, e.g. amplitude, phase, step response, pulse response.

Accordingly, with the proposed procedure no redundancy is created, which always consists of increasing, in the statistical sense, the reliability of the overall measuring operation by a plurality of the same type of measurements, but a test result is created only by using different analysis techniques, e.g. in a X-, Y-, Z-coordinates system three measurements each for X-, Y- and Z-position coordinates define the result, i.e. the position vector.

With the procedure according to the invention the selection method and the measuring arrangement used for this become extremely reliable in that, in particular, no containers are selected as admissibly contaminated when they are inadmissibly contaminated. The greater the number of independently used analysis techniques, the greater the aforementioned reliability becomes.

Because it is possible to carry out the different analysis techniques in parallel, i.e. simultaneously or quasi-simultaneously, there is no significant slowing down of the selection method on the gas inside or outside the respective container. As already mentioned, this is of decisive importance for containers that quickly succeed one another during in-line examinations.

According to the invention, gas analysis techniques that can be used are: infra-red absorption measurement, measurements by means of semi-conductor gas sensors, measurements by means of electrochemical cells, ionization, especially photo ionization and/or spark ionization, and measurement of the resultant gas ionization, or possibly measurement by means of mass spectroscopy. Preferred, because of the simplicity and rapidity, is the measuring combination by means of semi-conductor gas sensors, photo ionization and spark ionization. It is also readily possible to use, within the framework of the present invention, differently responding semi-conductor gas sensors in the sense of two different analysis techniques, and/or to use, in the indicated sense, the photo ionization or spark ionization or another of the mentioned analysis techniques twice or several times with different output signals in the sense of the present invention.

The group of preferred techniques also includes the infra-red absorption measurement, e.g. with infrared semi-conductor sensors, as marketed, for example, by the firm Kohl Sensors Incorporation, 70 W Barham Avenue, US-Santa Rosa, which, fitted with narrow-band, optical filters and when providing an infra-red transmitting source that gives off light in the IR-range in question, determine whether on predetermined absorption bands the transmitted radiation is absorbed or not by the gas, based on which a specific conclusion is reached regarding the presence or absence of specific substance contaminations and their concentrations.

Although with certain containers with container walls that transmit in the IR waveband in question, an IR absorption measurement could be carried out by irradiating the container, also then the transmission conditions of the container wall are subject to such great specimen dispersions that a reliable detecting of the said substance contamination in the gas is not readily possible. For the reason, with this procedure, i.e. when choosing the IR absorption measurement as one of the analysis techniques, the gas is subjected to the test as a gas sample, or, using light conductors on a lance IR-light is beamed into the container, recorded on this lace after traversing a gas path, and a corresponding signal is tapped off for the evaluation.

Furthermore, it is proposed to provide, with particular preference, as one of the analysis techniques at least one semi-conductor sensor, in particular a semi-conductor gas sensor, which ensures the use of a particularly simple analysis technique.

As a matter of fact, semi-conductor gas sensors are known, as made and marketed, for example, by the company Figaro Engineering, Osaka/Japan. Such semi-conductor gas sensors can be introduced extremely easily and, because of their small size, also directly into the containers or alongside a flow path for test gas from the containers, at any point, for the analysis of the gas samples. Under the aspect of reliability, by providing one or several such semi-conductor gas sensors it is possible to also realize with such sensors different analysis techniques in the sense of the present invention, or to create higher redundancy.

However, semi-conductor sensors, and in particular semi-conductor gas sensors have relatively long step response times, i.e. when a sudden change in the gas occurs on the input side, its output signal changes similarly to that of a low-pass filter, and relatively slowly moves asymptotically towards the corresponding end value.

This problem, which from the point of view of the rapidity of the process formed an obstacle for the use of semi-conductor gas sensors, is eliminated if the output signal of the at least one semi-conductor gas sensor is differentiated with respect to time, and the result of this differentiation, i.e. the initial signal climb is evaluated for the selection.

Since as output signal with such semi-conductor gas sensors usually the output resistance varies, the change with respect to time of its output resistance is, therefore, evaluated.

As the time differentiation of the semi-conductor gas sensor output signal correlates with the maximum value of the output signal which it tries to reach, already shortly after there occurs on the input side a change in a gas concentration and/or in a substance, the selection-effective signal can be ascertained from the said differentiation.

From the above it can now be noted, among others, that when a semi-conductor gas sensor has detected a gas contamination which moves its output signal in the direction of a new end value, this gas sensor, because of its "memory", will now analyse a further gas sample falsified with the result of previously detected measurements. This would mean that a provided gas sensor would again drastically slow down the process cycle, as it is necessary to wait until the effect of a previous gas analysis has died away.

This is prevented in accordance with the invention in that at least two sets comprising at least one semi-conductor gas sensor each are provided, and the test gas from successive containers if fed to different sensor sets, so that the individual sets are given time to re-set their output signals to a basic value without increasing the time of the process cycle from container to container.

So that, when proceeding in this manner, the supply lines and the semi-conductor gas sensor itself can be cleaned, with the method of the invention after a measurement the semi-conductor gas sensor, and therefore also the supply lines, are rinsed with a rinsing gas. With such a gas rinsing, because of the type of the rinsing gas and/or its flow along the sensor, there occurs on the sensor a behaviour similar to that which occurs during the aforementioned detecting of a contamination. As a result thereof such a gas sensor, because of the rinsing operation, again cannot be used for some time for contamination measurements.

The type of rinsing gas and/or the rinsing gas flow are adapted to the flow of uncontaminated test gas from the container in such a way that, when changing over from rinsing to measuring or vice-versa, this change produces an only minimal, if any, change in the signal at the output of the semi-conductor sensor. Accordingly, the sensor does not "experience" a change from testing cycle to rinsing cycle or vice-versa when the gas fed in during the testing cycle is not contaminated.

In accordance with the invention the gas can be removed from the container preferably using a carrier gas. The carrier gas is also used as rinsing gas.

By adjusting the flow of rinsing gas and the flow for gas from the container during the change-over rinsing-/measuring and vice-versa, the output signal of the semi-conductor sensor is kept substantially constant.

From the EP-A-0 306 307 mentioned at the outset it is known to examine the gas sample from a container by flame ionization followed by an analysis. This is a relatively slow process and in addition also disadvantageous from the simplicity point of view. On the one hand, as a matter of fact, during the flame ionization with a hydrogen flame, the gas flowing past the flame may not significantly disturb the flame, which sets limits on the flow velocity and therefore the rapidity of the measuring operation, and furthermore the supplying of flame gas is expensive.

For this reason, in accordance with the invention, as one analysis technique the gas is preferably exposed to an electrical discharge gap and its discharging behaviour and/or the discharge-related gas ionization is evaluated as an output signal for the selection. The providing of an electrical discharge gap, similar to the spark plug of a combustion engine, is extremely simple as this can be miniaturized, is not susceptible to contamination and, being flexible, electricity can be supplied to it practically anywhere. The measuring operation with this is very quick as it is at least within limits independent of the flow velocity of the test gas, and for certain applications the spark ionization, unlike the flame ionization, can be used in the to be tested container itself.

If, as one analysis technique, the gas is ionized within the framework of the analysis techniques of the method, a simple evaluation is realized by measuring the mobility of the ions.

A preferred embodiment of the method according to the invention is characterized in that with each of the analysis techniques, using calibrated gas samples, in a n-dimensional state space with $n \geq \neq 2$, with coordinates that each correspond to the output signals of the analysis techniques, at least one area is defined, with points corresponding to coordinate values which define admissible contaminations, and points outside the at least one area which define a gas state corresponding to inadmissible contaminations. The output signals ascertained on the gas by means of the techniques are automatically evaluated, as coordinate values, to determine whether they jointly define a gas state within the admissible area or not.

The gas state is, therefore, ascertained by means of a "state vector" and it is evaluated whether this state vector lies in an admissible or inadmissible range.

To furthermore prevent with to be tested containers that dominant gas portions or gas portions that are present in too high a concentration will make the subsequent analyses difficult, and to therefore reduce the concentrations in question to such an extent that the provided analysis techniques can operate in the provided ranges of measuring characteristics, it is proposed that at least prior to the use of at least one of the analysis techniques the containers are rinsed, preferably with water, steam, or gas, preferably air.

Prior to the use of at least one of the analysis techniques the containers can also be heated, preferably by means of infrared, steam, water, a gas, air or by means of microwave energy. If, the container is heated, it becomes possible to expel into the gas to be tested contamination components that have been absorbed by the container wall.

Furthermore, with the said selection there frequently exists a problem in that the original filling, also after emptying the container, produces or may produce such a high degree of contamination that this conceals other contaminations, in the sense of a signal-to-noise reflection. It would, therefore, be extremely advantageous if a simple, reliable procedure could be found for ascertaining what was the original content of a container.

This is achieved by the procedure of the invention wherein before using up the original content the containers are marked with a marking corresponding to their original content, and during the selection the marking is read and also used for the selection.

As a result thereof the analysis work is reduced in that, by reading the indicated marking, the original content becomes known and corresponding contaminations can be selectively suppressed or taken into consideration in favour of other contaminations or the corresponding signal portions.

With the aforementioned semi-conductor sensors, in particular semi-conductor gas sensors, the "memory" behaviour of which has been explained, there also occurs a special problem when one or several of the semi-conductor sensors detect a high contamination value that pushes up its output signal, so that such a sensor then also requires a correspondingly long time to swing back to its original value. As a result thereof such a semi-conductor sensor would then again not be ready for subsequent examinations, and the examination cycle would be extended accordingly until the said semi-conductor gas sensor has again reached its readiness to measure.

To prevent this, the output signals of the provided semi-conductor sensor sets are tested to see whether they exceed a predetermined value. If so, the set in question is disabled at least for immediately following analysis. One of the other semi-conductor sensor sets which is ready to measure is then used.

With the preferred time differentiation of the output signals of the semi-conductor sensors, naturally the time differentiation of this signal is tested to see whether it exceeds the predetermined value, so that also here one need not wait until the output signal of the semi-conductor sensor levels out on the output signal level that corresponds to the contamination.

Since anyway, preferably and according to the invention, successive gas samples are fed sequentially to different semi-conductor sensor sets, so that, for example, those that have just been used can in the meantime be rinsed, in the cases mentioned here preferably more than one measuring cycle is left out until the set which is over-saturated in the indicated sense is again ready to measure, which can easily be determined by monitoring its output signal, whilst the subsequent measuring cycles are carried out unaffected on other sets.

As was mentioned more towards the beginning, a preferred analysis technique used in connection with the present invention consists of the use of electrochemical measuring cells, as marketed for example by AMS Analysen-Mess-Systemtechnik, D-Dielheim, by means of which, the presence or absence of specific gas components can be detected within a narrow band.

The measuring arrangement according to the invention as referred to above is described in more detail hereinafter.

A test plant according to the invention with a measuring arrangement according to the invention is specified in claim 31, comprises a conveyor arrangement for plastic bottles that are conveyed as containers in streamline fashion to and from the measuring arrangement, and with which every bottle can be tested with great reliability and in a fast rhythm, unlike spot checks which, in particular in connection with the re-use of food containers, cannot be used for reasons of safety.

BRIEF DESCRIPTION OF THE DRAWINGS

In the following the invention will be explained, by way of example, with reference to figures.

These show.

DETAILED DESCRIPTION OF EMBODIMENTS

As mentioned at the outset, the present invention relates to the problem of investigating the state of contamination, in particular of empty containers. For example, with plastic bottles which are received for re-use, there exists great uncertainty as to how they were used after their original content, e.g. mineral water, fruit juices, etc., had been emptied. It is known that such bottles are often used for other purposes, for example in the household, e.g. for storing soap water, herbicides, engine oil, acids, petrol, benzene etc. If such substances were stored in containers that are made available for re-use with a new original filling, with certain categories of contamination substances an adverse effect on the taste of the newly filled original content can be expected, or such a container can no longer be used for re-filling because of the incompatibility of the contamination or because they may be harmful to people's health.

For this reason it must be ascertained whether and which residual contaminations are present in the containers, so that a selection can be carried out between containers that can no longer be used for a new original filling, those that, for example, first have to undergo a special cleaning process, and those that can quite safely be re-filled.

In this connection it must be borne in mind that, depending on the material of the container, in particular with plastic bottles, certain of the mentioned contamination substances are absorbed by the wall material, and the contamination is slowly desorbed into a freshly filled content.

As in certain cases also the content of a container may be contaminated, and the gas lying above this is then contaminate,d the invention can, with regard to all its aspects, also be used on containers that have already been filled. The procedure according to the invention is explained with reference to FIG. 8. Here, a combination of different analysis techniques is used, and their output signals are evaluated combined.

First of all, with reference to FIGS. 1 to 7, 9, preferred analysis techniques are described which, performed according to the invention, are especially suitable for the intended use within the system according to the invention.

Figure 1:
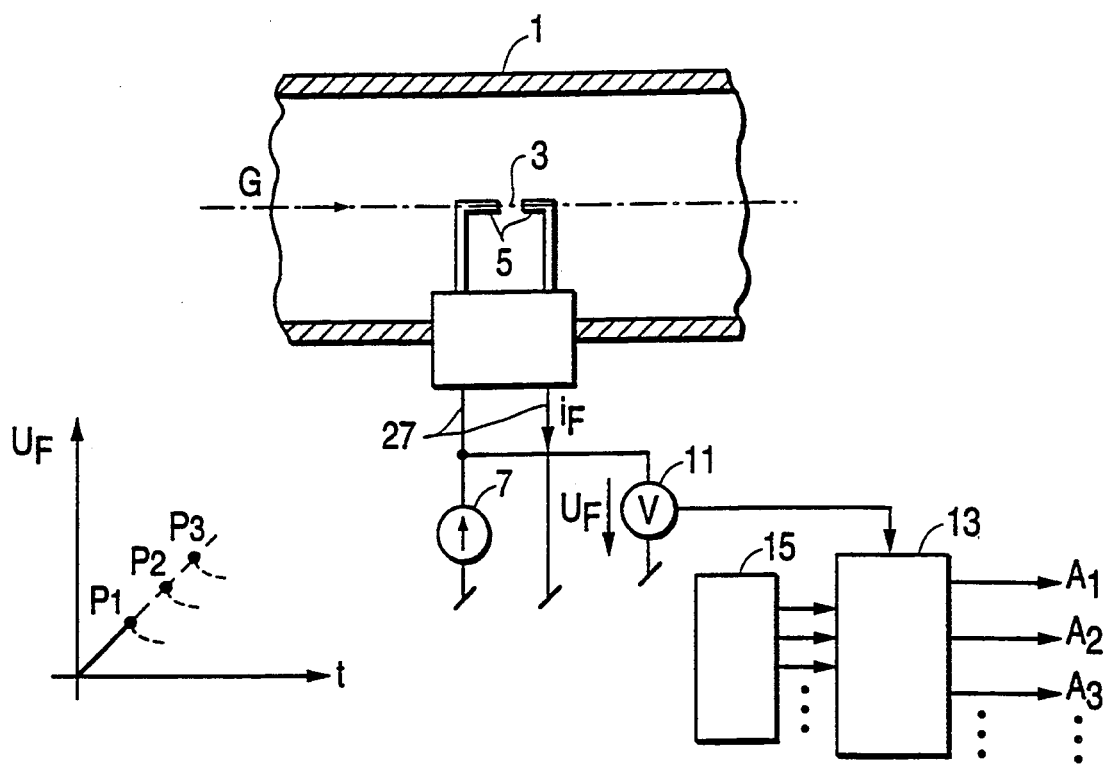
FIG. 1 diagrammatically a discharge gap used preferably as one of the gas analysis techniques with the method according to the invention or on the measuring arrangement according to the invention for the ionization and simultaneous determination of a measurable variable that is at least co-significant for the container selection according to the invention.

FIG. 1 shows diagrammatically an embodiment of a device for ascertaining a measurable variable which at least is co-significant as to whether the gas present in a container does or does not contain contaminations in a corresponding concentration of a specific substance group.

By way, for example, of a sampling line 1, a gas sample G is drawn off from a not illustrated, empty or partially filled container, possibly also one from outside the container which is in direct contact therewith or with its filling, and is moved past a discharge gap 3 with an electrode pair 5. The gap 3 is operated by means of a current source 7. The discharge is produced as a corona discharge or a spark discharge.

Figure 11:
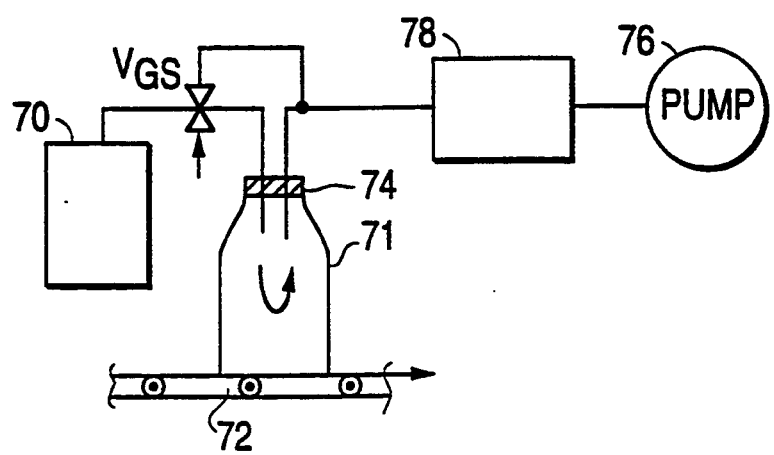

If, by the not illustrated suction device—in this connection see FIG. 11—the gas sample G is sucked up from the container and moved past the discharge gap 3, its discharge voltage will change. This voltage $U_F$ is measured with a voltage measuring device 11.

The output signal of the voltage measuring device 11 is evaluated as a measurable variable and to this end is fed, for example, to a comparator unit 13, to which other reference signals can be fed by a reference signal unit 15. Selected according to the discharge voltage $U_F$, output signals $A_1, A_2 \ldots$ are given off as measurable variables, which are relevant for specific sub-groups of contamination substances or even for specific contamination substances, or for specific contamination concentrations. The reference signals are determined by calibration measurements and are adjusted based on standard contaminated gas samples. In the diagram on the left in FIG. 1 the voltage $U_F$ is illustrated qualitatively with points $P_1$–$P_3$ corresponding to $U_F$-values at which the spark gap ignition takes place independently of the various contaminations acting thereon.

Figure 2:
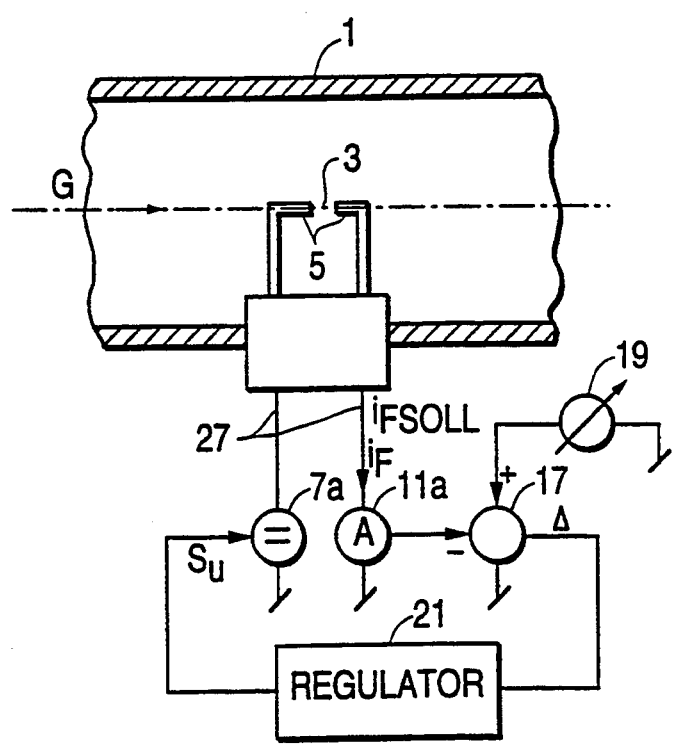
FIG. 2 proceeding from the illustration of FIG. 1, a further embodiment wherein the discharge current is regulated and the said measurable variable is determined from the behaviour of the regulating circuit, FIG. 3 diagrammatically, the use of the discharge gap for the ionization of the container gas in the container itself, FIG. 4 diagrammatically, an embodiment for the discharge ionization of the gas and subsequent, electrostatic ion separation, for determining a measurable variable as a preferred analysis technique or detector device, FIG. 5 analogously to the illustration of FIG. 4, a further embodiment, wherein ion separations are detected in dependence on respective ion mobilities as measurable variables, FIG. 6 diagrammatically, for use inside a to be tested container, a discharge ionization device, followed by an electro-static, mobility-selectively operating ion separation device, FIG. 7 diagrammatically, the provision of a pre-selection to prevent explosions in the case of certain contamination substances and with an electric discharge gap inside, (a), or outside, (b) the container, FIG. 8 under the main aspect of the present invention, a signal flow/function block diagram of a selection device according to the invention, operating by the method according to the invention, FIG. 9 a signal flow/function block diagram of an analysis unit with semi-conductor sensors, in particular semi-conductor gas sensors, FIG. 10a the qualitative response behavior of a semi-conductor gas sensor to rinsing gas/test gas cycles, FIG. 10b the adjusted behaviour of the semi-conductor gas sensor, FIG. 11 diagrammatically, the block diagram of a gas sampling unit.

Proceeding from the illustration of FIG. 1, FIG. 2 shows a further measurable variable determination on a discharge gap 3. Here, by means of a controllable high-voltage source 7a, a discharge is maintained between the electrodes 5 of the spark gap 3. With a current measuring device 11a, the discharge current $i_F$ is measured and compared on a comparator unit 17 with a current reference value $i_{FSOLL}$ that can be set on a reference signal unit 19.

The difference signal $\Delta$ ascertained on the comparator unit 17 is passed on as regulating difference, possibly by way of a regulator 21, as adjustment variable, to the controllable voltage source 7a which now acts as an adjusting element in the current regulating circuit, in such a way that the discharge current $i_F$ follows the reference value that can be set on the reference signal source 19 as nominal value adjuster, and preferably corresponds to the constant adjusted reference value $i_{SOLL}$.

The regulating difference signal $\Delta$ or the adjustment signal $s_u$ for the voltage source or the output voltage of the voltage source 7a is evaluated as measured variable. This measured variable is, as explained with reference to FIG. 1, fed in turn to a comparator unit 13 with superposed reference signal unit 15, and depending on the signal range in which the measured variable ascertained on the regulating circuit lies, a conclusion is reached regarding the presence or absence of contaminations of various substance groups or regarding the presence of contaminations of various concentrations in the gas sample G.

As can be noted from FIG. 1 and 2, here the discharge behaviour of the discharge gap 3 and its electric actuation is used directly as a test value for the measurable variable.

With the embodiments according to FIG. 1 and 2, a corona-AC or DC discharge is produced.

As illustrated in the FIG. 1 and 2 and 11, the gas sample G can be tapped off through a sampling line 1 from the to be tested container.

Figure 3:
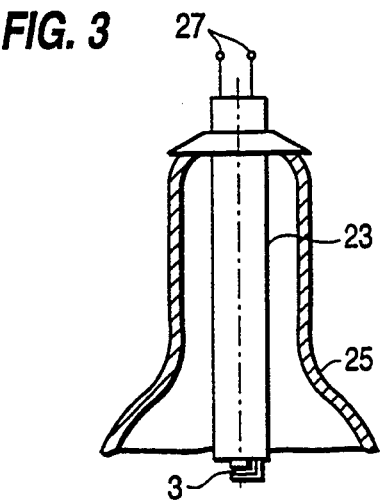

However, according to FIG. 3 it is also possible, seeing that the discharge gap 3 can easily be miniaturized, to introduce the discharge gap 3a into the to be tested container 25, e.g. with the aid of a test lance 23 illustrated diagrammatically in FIG. 3, and to then proceed in accordance with the information furnished in respect of FIG. 1 and 2.

The taps 27 on the lance 23 according to FIG. 3 correspond to the taps which in FIG. 1 and 2 are shown with the same reference numeral 27 on the discharge gaps 3 illustrated there.

Figure 4:
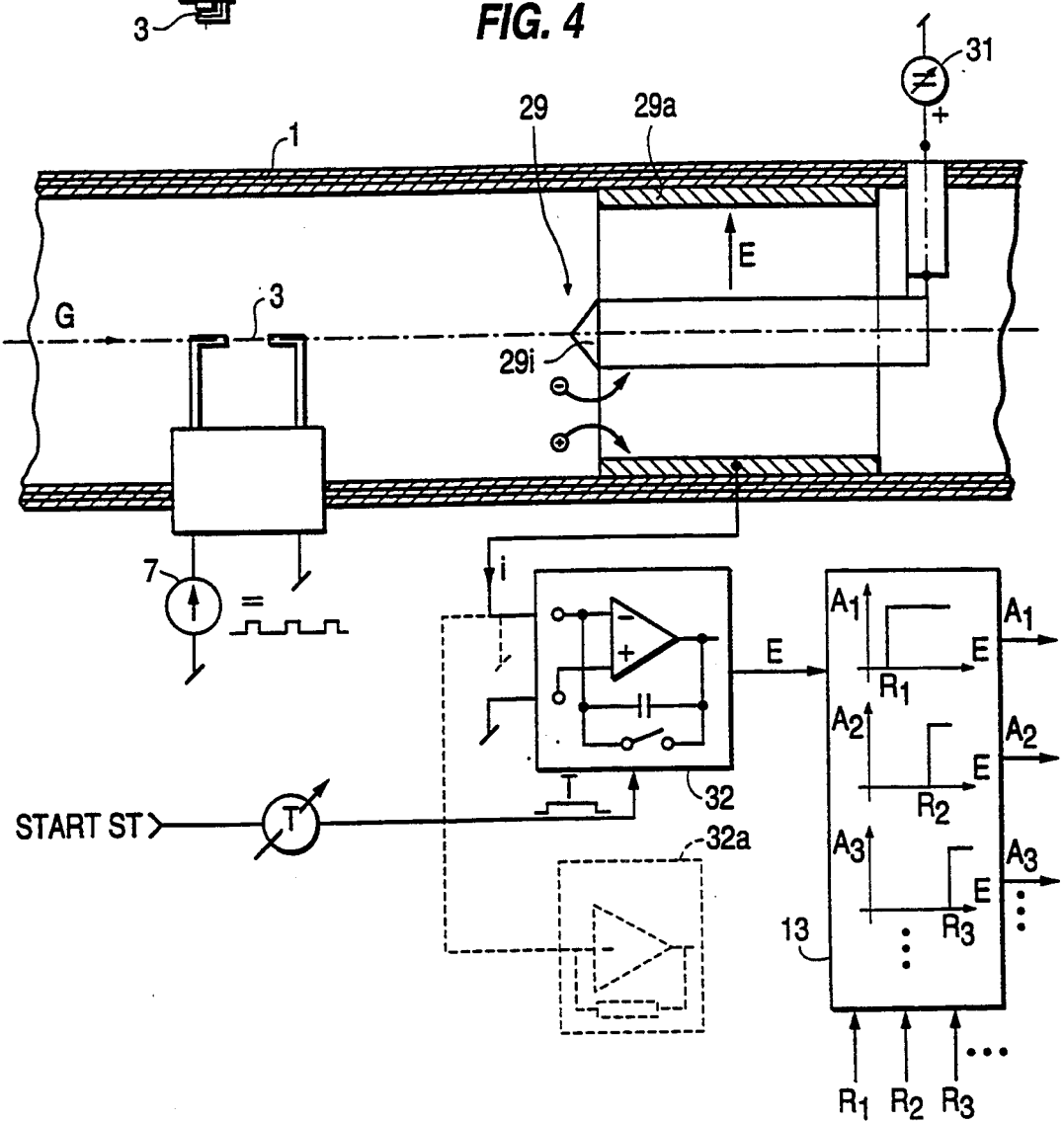

FIG. 4 shows a further embodiment of an arrangement used according to the invention for performing the method according to the invention, wherein by means of the discharge gap the gas is ionized and, in contrast to the embodiments of FIG. 1 and 2, the ionized gas is examined away from the discharge gap.

By way of the sampling line 1, the gas sample G is taken from the to be tested container or its direct vicinity and fed to the discharge gap 3, operated with the current source 7. A condenser arrangement, e.g. a cylindrical condenser 29, is provided after the discharge gap 3, in the direction of flow of the gas.

It comprises the cylindrical outer condenser shell 29a and the coaxial, inside mandrel 29i.

The condenser 29 is charged to a predetermined voltage value by means of an adjustable voltage source 31, so that an electric field E is formed on the condenser. Because of the gas ionization on the discharge gap 3, depending n the polarity and strength of the electric field E, ions of the one polarity are driven to one of the condenser plates 29a, 29a, and ions of the other polarity to the other plate. The balance of the ions driven to the capacitance plates 29a, 29i produces, in the external circuit connected to the cylindrical condenser 29, a current i. This is measured as current integral by a charge amplifier 32 or, as indicated by broken lines, by a current amplifier 32a.

When a charge amplifier 32 is provided, the integration time T, during which the current flowing through the condenser 29 is integrated, is pre-set, and this interval T is set off by any signal ST defining the start of the measuring cycle, e.g. at the start of the sucking off of gas or when a specific surge front of the current i occurs.

When the integration time T has expired, the re-setting switch on the charge amplifier—illustrated diagrammatically in FIG. 4—is closed.

The output signal, whether it corresponds to the current integral, if the charge amplifier 32 is provided, or to that of the provided current amplifier 32a, is fed, in the manner already described with reference to FIG. 1, to a comparator unit 13, on the output side of which, selected according to the magnitude of the occurring input signal E, output signals $A_1$, $A_2$ etc. occur as a measurable variable.

Here the spark gap 3, arranged either in a to be tested container itself in accordance with FIG. 3, or, as illustrated in FIG. 4, in the sampling line 1, is used only for the ionization of the to be tested gas.

This procedure makes it possible, because the discharge gap can be miniaturized, to provide the gas ionization in a constructionally flexible manner at any point of a selection plant. The separation takes place at the same place, either along the sampling line, or in the to be tested container itself, or the position thereof is located away from the ionization.

Figure 5:
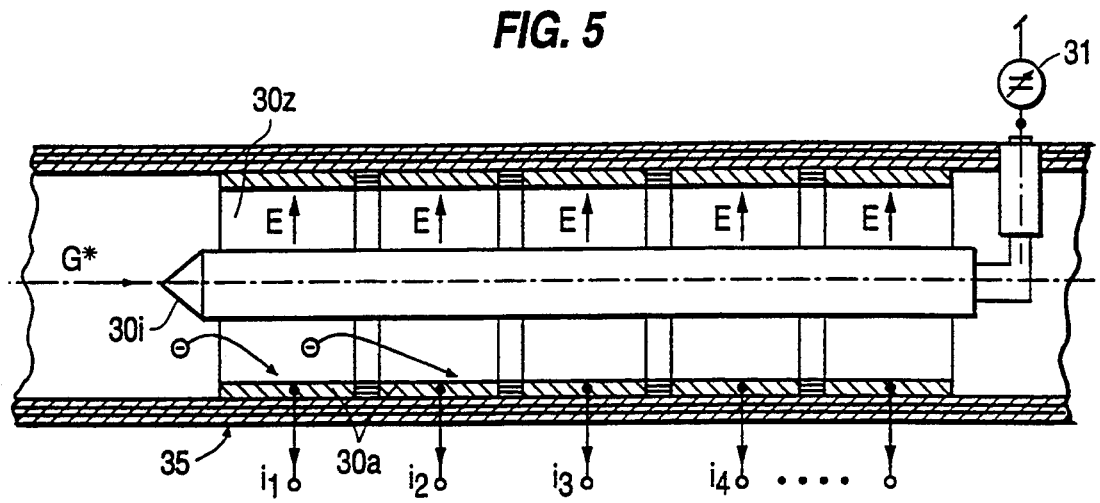

Whereas the procedure described with reference to FIG. 4 only permits a lump sum determination of, as measurable variable, the charge balance of the gas that occurs as a result of the spark ionization, to which end, if the condenser arrangement 29 is arranged alongside a sampling line 1, the gas must be fed in at a predetermined flow velocity, FIG. 5 shows in principle a procedure by means of which, after ionization of the gas from the container, either by the use according to the invention of a discharge gap, or also in the known manner, e.g. by flame ionization or, preferably, photo ionization by means of UV, an evaluation takes places of the ions formed in the gas according to their mobility. As a result thereof contaminations of different substances or substance groups can be detected more selectively.

To this end the ionized gas G* is fed to an electrostatic separator stage 35, constructed substantially as shown in FIG. 4, which, for example, again consists of a cylindrical condenser arrangement. This comprises, for example, a large internal mandrel 30i as well as a plurality of cylindrical surfaces 30a arranged insulated behind one another. All condensers, formed by the common internal mandrel 30i and one cylindrical surface 30a each, are preferably placed under the same electro-static voltage by means of the voltage source 31, so that the same field strengths E lie above the respective condensers 30a, 30a.

If the gas enters the condense space 30z with ions of a different mobility, as illustrated diagrammatically, and these experience in same, because of the homogeneous field strength E, provided that the ions have the same charges, also identical deflection forces, then the more mobile ions are deflected more per axially traversed path than the less mobile ones. Accordingly, the currents $i_1, i_2$ ... led off from the respective condensers are, as measurable variables, an indication for the ions deflected sequentially in the direction of the gas flow, wherein ions of a decreasing mobility contribute an increasing amount to the current of the condenser arrangements positioned downstream with respect to the direction of flow of the gas.

The tapped-off currents i, as explained with reference to FIG. 4, are detected by a charge amplifier or current amplifier, and processed further as measurable variables for the container selection.

Figure 6:
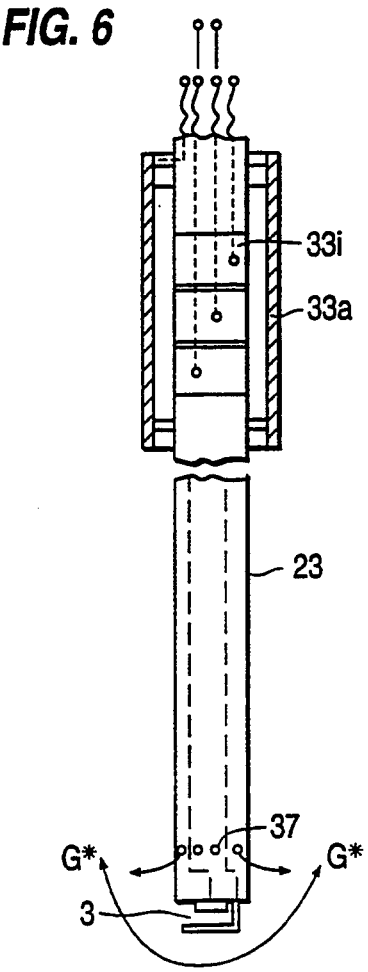

FIG. 6 shows an embodiment for discharge ionization of the gas and electro-static separation measurement, directly in a to be tested container. In a further development of the arrangement described with reference to FIG. 3, on the lance 23 at its end there is a discharge gap 3, and on the upper part, a plurality of metallic surfaces 33i, insulated from one another, are provided, and coaxially to same, a metallic cylindrical surface 33a is provided.

As illustrated diagrammatically, the lance which has been developed further in this manner is let into a to be tested container, and near the bottom thereof the gas is ionized by means of the discharge gap 3. Already because of the resultant heating of the gas inside the container, there occurs a gas flow in the direction of the container opening, in which section lies the separator stage formed by the condensers 33a, 33a.

Preferably, in addition to this, a forced flow of the ionizing gas G* is brought about by feeding in a further gas, a carrier gas, e.g. through diagrammatically illustrated openings 37.

The electricity supply to the spark gap 3 and the condenser arrangement as well as the current taps for tapping off the currents $i_1, i_2$ etc. are passed through the lance 23, and the same applies to a line to the gas outlets 37.

As mentioned, with the embodiments according to FIG. 1 to 3 preferably a corona discharge is produced. With those according to FIG. 4 to 6 both a corona discharge as well as a spark discharge can be produced, i.e. when the ionization of the gas is measured. When operating with spark discharge, for a measurement, preferably a series of a predetermined number of sparks is produced, and in the flowing gas G* ionized by this the ion density is measured and averaged over a predetermined period, so as to obtain, in particular, more reliable results.

With certain contamination substances the discharge ionization according to the invention, or also a known flame ionization, may cause an explosion. Because of this, for reasons of safety, when using these ionization techniques on the occurring empty containers, a preselection must be carried out. This is, for a measuring inside the container, illustrated diagrammatically in FIG. 7a. According to this the to be tested containers, e.g. plastic bottles, are moved on a conveying installation, either a conveyor belt or a carrousel system, past a first measuring station 40, where, either by the taking of gas samples, as illustrated, or by immersing a probe into the container in question, the presence of specific, explosive contaminations is detected.

To this end, according to the invention preferably semi-conductor gas sensors or electro-chemical cells are used, adapted to the detecting of known explosive contaminations. If a container with explosive contaminations is detected, then, as illustrated diagrammatically, e.g. by means of a conveyor shunt, the container in question is removed so that it will not be tested further. Containers that are recognized as safe in this respect are passed on to the ionization measuring station 42 with the lance 23.

Based on the ascertaining of further contaminations and a corresponding evaluation of the relevant measuring signals on an evaluation unit 44, a further conveyor shut is actuated, and inadmissibly contaminated containers are removed or passed on to a special cleaning process, whilst only containers with contaminations of an admissible type are passed on for re-filling.

As was mentioned at the outset, certain contamination substances are absorbed by certain wall materials of the containers, and in particular by plastic, and are released again into the inside of the container only slowly and in dependence on the temperature. Without special measures the contamination concentration inside the container, viewed at a given time, may be difficult to measure. However, if the container has been filled and has been stored for quite a long time, there nevertheless occurs, for example, an adverse effect on the taste of the content of the container.

Figure 7A:
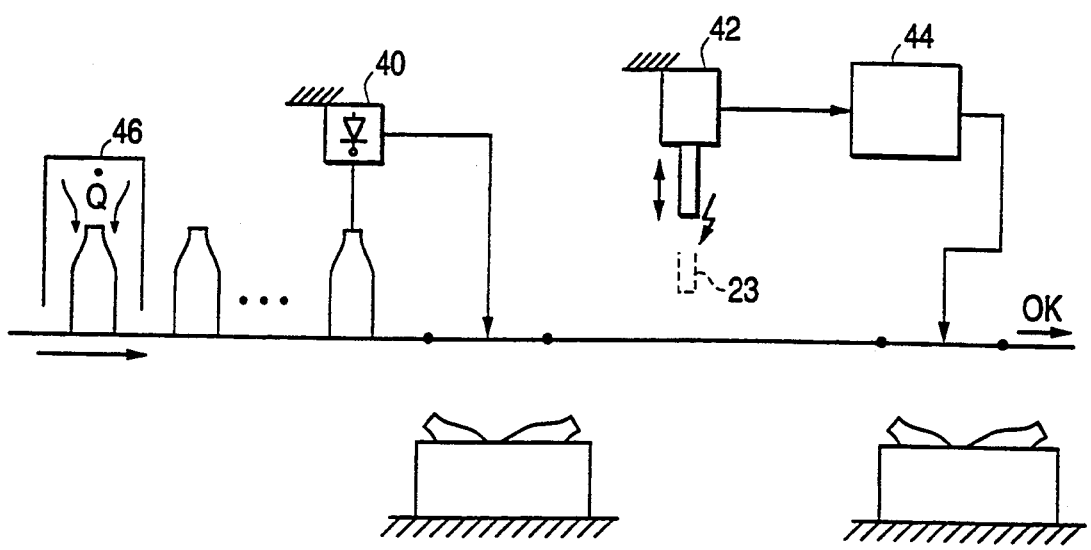

It is, therefore, furthermore proposed, as illustrated diagrammatically in FIG. 7a at 46, that prior to carrying out the contamination detection, contamination substances that have been absorbed by the walls of the containers should be expelled. According to the invention, this is done by heating the containers, as illustrated by the heat flow Q, which can be done by infrared radiation, and with plastic containers in particular also by microwave heating, by vaporization or gasification of the inside of the container and/or from the outside, e.g. by letting in normal hot air.

In certain cases it is anyway indicated to rise the containers with a gas, preferably with air, in particular purified air, and to rinse out certain amounts of residual gas stemming from specific original contents, which otherwise could conceal other contaminations during the contamination detection.

Contaminations stemming from original contents, e.g. from fruit juices, can, as was found, cause considerable interference during the detection of other contamination substances. An extremely simple possibility for overcoming this problem consists in providing the containers with a marking, e.g. a moulded-in code, corresponding to the original content. If this is provided, such a marking can easily be read during the selection of the empty containers, so that information is then at hand regarding the type of the original content.

In accordance therewith, contamination signals can be filtered out in a narrow band, adjusted to this one product, so as to reduce the measuring interference caused by the original content.

In this way the problem of the original content-related measuring interference can be solved, for the making available of measurable variables for the container selection discussed here.

As has already been mentioned, the main problem in achieving the objectives set here is that most analysis techniques, unless one goes to great expense, e.g. by selective infrared spectrography or by using expensive mass spectrometers, supply measuring signals that are dependent on the type of the contamination substance as well as on its concentration. This means, in other words, that often there exists ambiguity as to whether a substance A with the concentration $\alpha$ is present or a substance B with the concentration $\beta$, as on the same "detector" both conditions may lead to the same output signal.

If one now looks at analysis techniques, which are
photo ionization or flame ionization followed by an ion density determination, spark gap ionization followed by a not further categorized ion density determination or ion density determination taking into account the mobility of the ions, detection of contamination substances with semi-conductor gas sensors or by means of infrared absorption measurement with semi-conductor infrared sensors, in principle possibly also mass spectroscopy, detection of certain contamination substances with electro-chemical cells, i.e. in the light of the container selection problem of the type discussed here, it will be noted that also if the above case occurs with the one technique, with at least one of the other techniques the signal for the contamination substance B with the concentration $\beta$ will not be the same as that for the substance A with the concentration $\alpha$.

By the combined use according to the invention of at least two of the mentioned techniques, as will be explained in the following, the selectivity reliability is, therefore, considerably increased, or rather is only now obtained.

Figure 8:
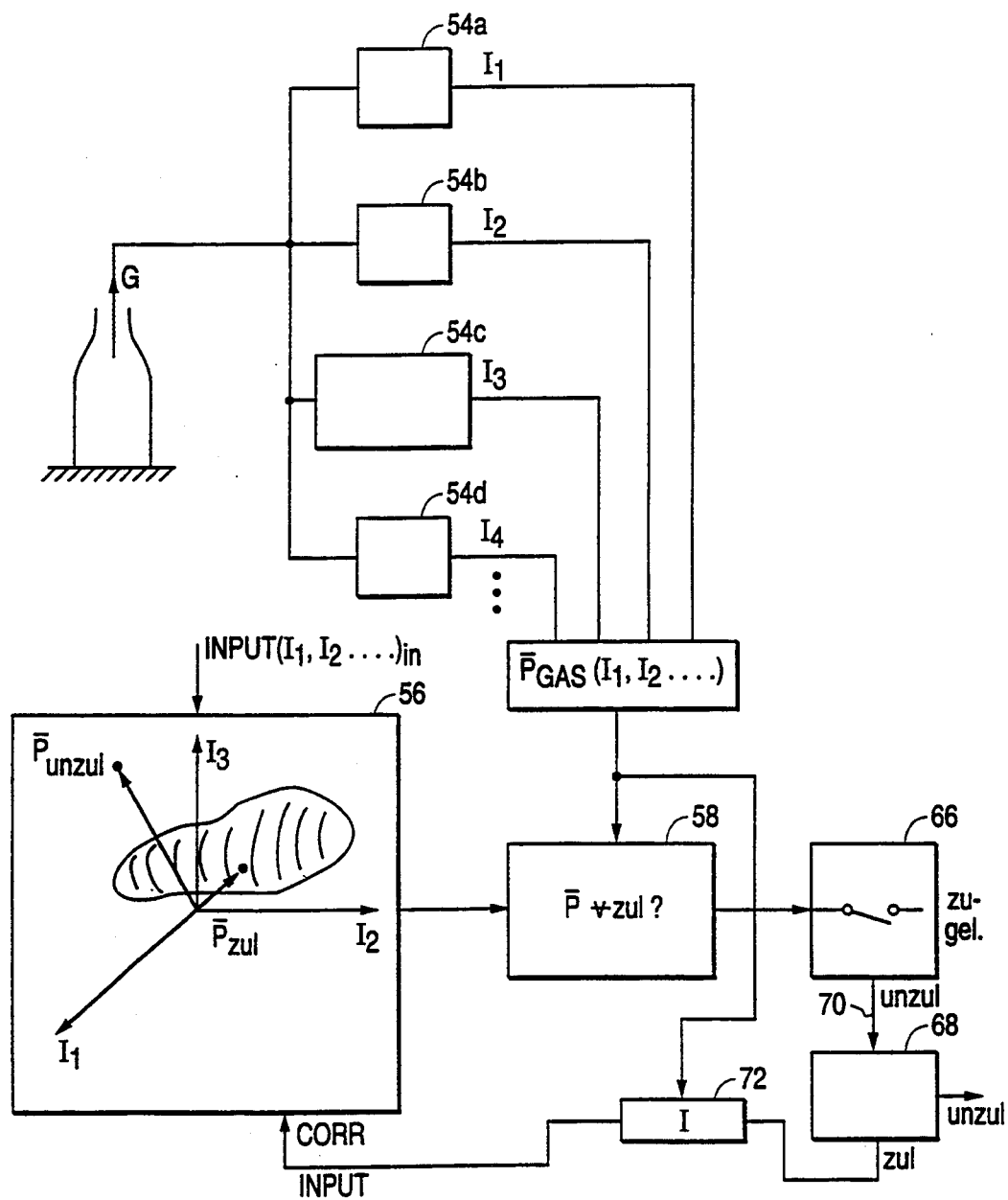

This takes place, according to FIG. 8, under the main aspect of the present invention, in that, as illustrated diagrammatically, gas from the to be tested container is fed to a number n of different analysis stations, with $n \geq \neq 2$, e.g., as illustrated, to a station 54a based on gas ionization, a station 54b based on the use of semi-conductor gas sensors, a station 54c based on the use of electro-chemical cells, a station 54d based on the use of infrared absorption measurement, etc., or also analysis stations of the same type, but with different measuring characteristics.

For a gas sample, the n stations produce measured values $I_1 \ldots I_n$ that are informative for the selection. These signals I define in a n-dimensional state space the state $\overline{P}$ of the gas in question.

On an evaluation computer a n-dimensional "space " is stored in a nominal range store 56, and in same state ranges that are admissible and that are inadmissible. This is illustrated diagrammatically in the block 56 in FIG. 8 in a three-dimensional "space" with the coordinates corresponding to $I_1, I_2, I_3$ and the admissible range ZUL. The values $I_1$ to $I_n$, which define admissible and inadmissible contamination compositions and concentrations of the gas, respectively, are ascertained beforehand by calibration measurements with standardized gas and stored in the store 56.

When measuring the state $\overline{P}$ of a gas occurring at a specific moment, the gas sample state defined by the measured values $I_1$ to $I_n$ is compared in a comparator unit 58 with the admissible state vectors $\overline{P}_{ZUL}$ for the gas sample, stored in the store 56. If the state vector $\overline{P}$ of the gas sample tested at that moment lies within the space range stored in the store 56, then on the output side of the comparator unit 58 the selection is decided in the affirmative sense, i.e. the container that has just been tested is released as acceptable for re-filling.

Otherwise the container in question is eliminated.

The input ZUL $(I_a, I_2 \ldots)_{in}$ on the storage block 56 represents the input for the ascertained coordinate values I, which define the admissible vector space range ZUL. Furthermore, after the selection on the selection block 56, on the path for inadmissibly contaminated containers, a further selection stage 68 may be provided, where, for example, without time pressure, it is checked once again under laboratory like conditions whether a container coming in on this path 70 is, in fact, inadmissibly contaminated or not. If it is really inadmissibly contaminated, it is eliminated. If not, its vector coordinate value I will be stored in an intermediate store 72, fed back to the storage block 56, to thus define in an automatic learning process the admissible space range ZUL in a more refined way.

Extremely suitable for such a procedure is a neuronal computer network, wherein an initial rough model, corresponding here to the admissible space range ZUL, is refined by an automatic learning process.

As was mentioned at the outset, one of the preferred analysis techniques is based on semi-conductor sensors. When using such semi-conductor elements there exists, as explained at the outset, a problem in that its step response is relatively slow. If, during the flowing past of contaminated gas, a contamination pulse is produced on the input side of such a sensor, the semi-conductor sensor output signal will move up relatively slowly to a corresponding maximum value, to then drop again just as slowly.

These problems may also occur with other measuring techniques, e.g. with the infrared absorption measurement with semi-conductor infrared sensors, so that the following explanations also apply to these.

As can be noted from FIG. 9, the output signals or the semi-conductor sensors 60a, 60b and 60c illustrated there are such that, depending on the occurring contamination, they move towards the maximum value $A_{max}$, which however takes relatively long.

To now generally shorten the measuring cycle time, use is made of the fact that the climb of the output signal increases when the reached maximum output signal value becomes higher. Because of this, with such sensors the sensor output signal is not evaluated directly, but its time differentiation 61 is evaluated as the measurable variable $A_n$, as illustrated in FIG. 9.

As with semi-conductor sensors the variable is its resistance. A corresponds to the resistance pattern.

As can furthermore be noted, the time which the output signal of such sensors requires to again assume its initial value is the loner, the higher the reached maximum value $A_{max}$. To now nevertheless be able to drastically shorten the measuring cycle time, independently of this, according to FIG. 9 two or much such sensors or sets of such sensors are used„ e.g. cyclically, for successive gas sample analyses. This is controlled by a control unit with a cyclic register 62. Preferably it is monitored, e.g. with the comparator units 64, whether the output signal of one of the sensors or set of sensors assumes an inadmissibly high value, and this one sensor or set of sensors is then taken out of the cycle for a predetermined time $\tau$.

Accordingly, sets 60a, b . . . of at least one semi-conductor sensor each are provided, which are used sequentially for successive gas samples G. If the output signal of a semi-conductor sensor or its time differentiation moves beyond a threshold value pre-set on comparator units 64, then the sensor or set of sensors in question will be switched off for a predetermined number of subsequent sample gas measuring cycles.

As illustrated by broken line,s in this connection it is readily possible to monitor the output signal values A, e.g. with a further comparator 65 indicated bay broken lines, and, as illustrated for set 60c, by way of example, to determine, in accordance with the momentary output signal value, the time during which a semi-conductor gas sensor set must remain switched off. In other words, such a sensor set will only again start to measure when its output signal value again drops below the threshold value set on the threshold value unit 65.

A further problem with semi-conductor gas sensors or possibly also radiation semi-conductor sensors, as used for the infrared absorption measuring, is that on the one hand supply lines for the sample gas and housing arrangements in which the sensors are arranged must be rinsed to minimize the influence of a preceding measurement on a subsequent measurement, but that on the other hand such semi-conductor sensors react to a rinsing gas flow with a slow output signal, of the type as illustrated at A in FIG. 9. This would mean, therefore, that when such semi-conductor sensors are rinsed, in particular rinsed with gas, preferably with purified air, after such a rinsing cycle they must remain out of operation for just as long as after a measuring cycle, i.e. the number of provided semi-conductor sensor sets 60 according to FIG. 9 would have to be doubled to obtain the same throughputs.

Figure 10A:
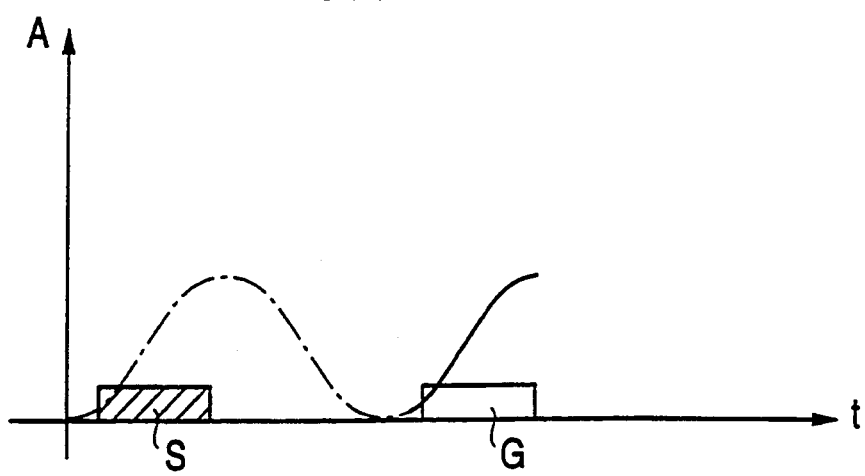

FIG. 10a illustrates qualitatively, over the time axis t, a rinsing gas flow S, hatched, and by dot-dash lines the resultant pattern of the output signal A of a semi-conductor gas sensor. From this it can be noted that only after expiry of a fall time, a new measuring cycle with the test gas supply G can be started on the semi-conductor gas sensor in question. However, for time-economy reasons, one should aim at letting measuring cycles immediately follow rinsing cycles and vice-versa.

Figure 10B:
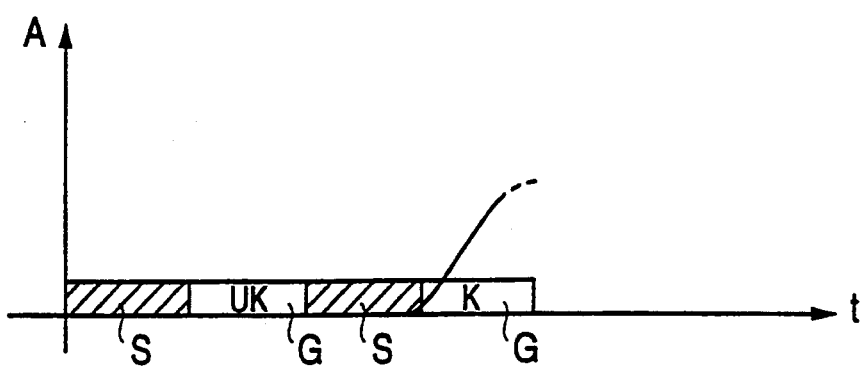

Accordingly to FIG. 10b in conjunction with FIG. 9, this now becomes possible according to the invention in that the test gas flow G and the rinsing gas flow S are adapted to one another by means of flow adjustment elements, as illustrated diagrammatically in FIG. 9 at $V_G$ and $V_S$, in such a way that the semi-conductor gas sensor experiences a substantially continuous, constant flow. With this, the test gas flow is preferably produced by the flow of a carrier gas, to which is added gas from the container that is being tested. Preferably, as rinsing gas the same gas is then used as the carrier gas, for example and preferably dry, purified air is used for both. If different gases are used for the rinsing and as carrier gas, it has been found that by changing the flow ratio of the test gas G and the rinsing gas S, the influence of the different gas types can to a large extent be compensated.

FIG. 10b illustrates diagrammatically, for identical carrier and rinsing gases, rinsing cycles S, a measuring cycle G with uncontaminated gas, i.e. carrier gas, then a measuring cycle G with contaminated gas. Taking into account the semi-conductor output signals, the adjustment is carried out such that during the successive cycles rinsing gas/carrier gas or uncontaminated test gas, essentially no output signal or possibly a substantially time-constant output signal appears on the semi-conductor gas sensors, which makes it possible to test and rinse successively in the sense indicated above.

The use of a carrier gas takes place, for example, as illustrated in FIG. 11, by connecting, e.g. by means of a sealing connection 74, a carrier gas tank 70 to the container 71, which is shown positioned on a conveying device 72. By means of a pump 76, carrier gas together with gas contained in the container is fed to the measuring arrangement according to the invention, as illustrated at 78. Naturally, it is also possible to utilize the water jet pump principle with the carrier gas as pump gas.

The use of the carrier gas as rinsing gas can take place, for example, in an extremely simple manner by providing a controllable change-over valve $V_{GS}$, by means of which the container is bridged during rinsing phases.

Furthermore, the multi-parameter evaluation explained with reference to FIG. 8 and the corresponding procedure can be modified as follows:

By means of sample gas measurements, divided into admissibly contaminated and inadmissibly contaminated, admissible and inadmissible combinations of the output signals $I_1$ to $I_n$ are ascertained. With these I-values ascertained on the calibrated gas samples, a suitable mathematical function is now determined, in such a way that the function value, in dependence on the mentioned variables, can be divided unequivocally into at least one value range for admissibility and value ranges for inadmissibility.

Instead of storing an admissible multi-dimensional range, as was explained with reference to FIG. 8, possibly to save storage space, the found mathematical function is stored, and the measured gas values are entered into this function as variables. After doing so, it is examined whether the resultant function value lies in the admissible or in the inadmissible function value range.

Figure 7B:
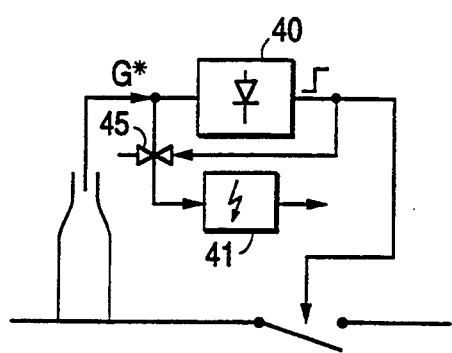

If furthermore, unlike FIG. 7a, a gas sample G* is taken from the container according to FIG. 7b, preferably the testing for explosive contaminations takes place on the gas sample in question before it is passed on to the unit 41 for the discharge or flame ionization. The station then controls, for example, a valve 45 provided ahead of the unit 41.

By utilizing various transfer characteristics, in particular also of the different, described analysis techniques, both with regard to contamination substances as well as their concentrations, it is made possible, by a combined consideration and evaluation of the measured variables of at least two of these stations with different characteristics, to ensure a considerably greater certainty as to whether a specific container can be used again or not. The signal controlling the selection is a uniform signal composed of various components.

We claim:

1. A method for automatically selecting substantially empty foodstuff containers for refilling or not refilling with foodstuff comprising the steps of:

extracting from a container a sample of gas;

leasing said sample to at least two gas analyzer detector means, said at least two gas analyzer detector means each providing an electrical output signal, dependent from component composition of said sample and of concentration of said component of said sample, the output signals of said at least two detector means being differently dependent from said component composition and from said component concentration;

determining whether each of said output signals is within a respective one of preselected and stored ranges of signals for each of said output signals; and selecting said container for refilling if each of said output signals is within its respective range.

2. The method of claim 1, wherein said detector means comprise at least one of the following detectors: infra-red absorption detectors, semi-conductor gas sensors, electro-chemical cells, and ionization cells.

3. The method of claim 2, wherein said ionization cells comprise at least one of photo-ionization and spark ionization cells.

4. The method of claim 1, wherein said detector means comprise at least one semi-conductor gas sensor, the output thereof being differentiated with respect to time to form an output signal of said detector means.

5. The method of claim 1, further comprising providing at least two sets of detector means, each of which comprises at least one semi-conductor sensor, and wherein said containers are conveyed in line for refilling gas samples from successive in-line conveyed containers being lead to different sets of said at least two sets.

6. The method of claim 1, comprising the step of providing at least one semi-conductor sensor for said detector means, rinsing said semi-conductor sensor with rinsing gas after exposure to gas of said sample, wherein the type of rinsing gas is adapted to the gas of said sample and/or the flow of said rinsing gas along with semi-conductor sensor is adjusted to the flow of the gas of said sample along with semi-conductor sensor for minimizing the influence of said rinsing gas on a subsequent detection behavior of said semi-conductor sensor.

7. The method of claim 6, wherein said sample of gas is combined with a carrier gas to form a combined sample which is lead to said at least two gas analyzer detector means, and wherein said carrier gas is the same as said rinsing gas.

8. The method of claim 7, including adjusting the flow of said rinsing gas and the flow of said sample of gas according to a container selected for refilling along said semi-conductor sensor so that changing from a rinsing to a selecting cycle or vice versa does not significantly alter the output signal of said semi-conductor sensor.

9. The method of claim 6 wherein said rinsing gas to purified air.

10. The method of claim 1, wherein gas analyses at at least one of said gas analyzer detector means is performed by exposing said sample to an electrical discharge gap and an output signal of the detector means is generated from at least one of electrical discharge behavior of said gap and/or discharge related ionization of said sample.

11. The method of claim 1, wherein gas analyses within at least one of said gas analyzer detector means is performed by gas ionization and generation of an output signal dependent on the mobility of the ions.

12. The method of claim 1, including rinsing said container prior to extracting said sample.

13. The method of claim 12, wherein said container is rinsed with at least one of water, steam and gas.

14. The method of claim 13, wherein said container is rinsed with air.

15. The method of claim 1, including heating said container prior to extracting said sample.

16. The method of claim 15, wherein said heating is by means of infrared radiation, steam, water, gas or by means of microwave radiation.

17. The method of claim 1, including marking the container when originally filled with a marking identifying the filling product.

18. The method of claim 17, further comprising detecting said original content by reading said marking and additionally using said reading for said selecting.

19. The method of claim 1, wherein at least one of said gas analyzer detector means comprises at least one semi-conductor sensor, and including the steps of checking the output signal of said at least one semi-conductor sensor to determine whether it exceeds a predetermined signal value and if it exceeds said predetermined signal valve disabling said semi-conductor sensor for analyzing at least an immediately following sample of gas.

20. The method of claim 1, wherein containers not selected for refilling are subjected to a further gas analysis, said signal ranges being automatically adjusted according to the result of that further analysis.

21. The method of claim 1, wherein said containers are beverage plastic bottles.

22. An apparatus for automatically selecting in-line conveyed foodstuff containers for refilling comprising:
conveyor means for conveying said containers;
gas sample extracting means arranged along said conveyor means for extracting a gas sample from each of said containers conveyed by said conveyor means;
a gas analysis arrangement, said extracting means being connected to said gas analysis arrangement, said gas analysis arrangement comprising at least two detector arrangements generating electric output signals, the electric output signal of each of said at least two detector arrangements being dependent from component composition of said sample and from component concentration, said at least two output signals being differently dependent from said composition and said concentration;
a comparator unit, the output signal of said at least two detector arrangements being lead to said comparator unit;
storage means for storage of at least two signal ranges for the output signals of respective ones of said at least two detector arrangements, the output of said storage means being lead to said comparator unit, each output signal of said comparator unit being dependent n whether said output signals of said at least two detector arrangements for a given container are both within their respective signal ranges stored within said storage means, and if so the container is freed for refilling.

23. The apparatus of claim 22, wherein said gas analysis arrangement comprises at least one of an infrared absorption measuring device, a measuring device with at least one semi-conductor gas sensor, a measuring device with at least one electro-chemical cell, a mass spectrometer, and an ionization device.

24. The apparatus of claim 23, wherein said gas analysis arrangement comprises at least one photo ionization and/or spark ionization device.

25. The apparatus of claim 22, wherein said gas analysis arrangement comprises at least one semi-conductor sensor arrangement.

26. The apparatus of claim 22, wherein said gas analysis arrangement comprises at least one semi-conductor sensor, the output signal of said semi-conductor sensor being lead to a time differentiation unit, the output signal thereof being one of said output signals of the detector means.

27. The apparatus of claim 22, wherein said gas analysis arrangement comprises at least two sets of detector arrangements with at least one semi-conductor sensor each and further comprising controllable switching means for switching selectively said gas sample to one or the other of said sets.

28. The apparatus of claim 27, further comprising a control unit for controlling said switching means so as to feed said samples intermittently to one of said at least two sets.

29. The apparatus of claim 28, further comprising a threshold value sensitive unit, the output of said semi-conductor sensors of said at least two sets being led to said threshold value sensitive unit, the output thereof acting on a control input of said control unit so that, when an output signal of one of said semi-conductor sensors exceeds a threshold value of said threshold value sensitive unit, the semi-conductor sensor generating said exceeding output signal is disabled at least for the subsequent gas sample analysis.

30. The apparatus of claim 22, wherein said gas analysis arrangement comprises at least one semi-conductor sensor, further comprising a rinsing gas line communicating with a rinsing gas source, said rinsing gas line opening in an area with said semi-conductor sensor.

31. The apparatus of claim 30, further comprising at least one slow-adjusting element for adjusting the ratio of rinsing gas flow to said semi-conductor sensor and the flow of gas of said sample to said semi-conductor sensor.

32. The apparatus of claim 22, further comprising a carrier gas feedline from a carrier gas source towards a container and a suction line for said carrier gas and gas from said container forming said sample, said suction line leading to said gas analysis arrangement.

33. The apparatus of claim 22, wherein said gas analysis arrangement comprises an ionization device.

34. The apparatus of claim 33, wherein said ionization device comprises a spark gap for ionization of said sample.

35. The apparatus of claim 33, further comprising at least two electrostatic ion separation stages arranged along a downstream flow path for said sample with respect to said ionization device.

36. The apparatus of claim 22, further comprising a code reading device for reading a code on said containers.

* * * * *